(12) United States Patent
Hartmann et al.

(10) Patent No.: US 12,161,657 B2
(45) Date of Patent: Dec. 10, 2024

(54) COMBINATORIAL THERAPY FOR USE IN INDUCING IMMUNOGENIC CELL DEATH IN CANCER CELLS

(71) Applicants: James Hartmann, Boca Raton, FL (US); Patricia Keating, Boca Raton, FL (US); Youssef Motii, Boca Raton, FL (US)

(72) Inventors: James Hartmann, Boca Raton, FL (US); Patricia Keating, Boca Raton, FL (US); Youssef Motii, Boca Raton, FL (US)

( * ) Notice: Subject to any disclaimer, the term of this patent is extended or adjusted under 35 U.S.C. 154(b) by 0 days.

(21) Appl. No.: 18/075,621

(22) Filed: Dec. 6, 2022

(65) Prior Publication Data

US 2023/0172956 A1    Jun. 8, 2023

Related U.S. Application Data

(60) Provisional application No. 63/286,367, filed on Dec. 6, 2021.

(51) Int. Cl.
| | | |
|---|---|---|
| *A61K 31/7004* | (2006.01) | |
| *A61K 31/352* | (2006.01) | |
| *A61K 31/519* | (2006.01) | |
| *A61K 45/06* | (2006.01) | |
| *A61P 35/00* | (2006.01) | |

(52) U.S. Cl.
CPC ........ *A61K 31/7004* (2013.01); *A61K 31/352* (2013.01); *A61K 31/519* (2013.01); *A61K 45/06* (2013.01)

(58) Field of Classification Search
CPC .............. A61K 31/7004; A61K 31/352; A61K 31/519; A61K 45/06; A61K 2300/00; A61P 35/00
See application file for complete search history.

(56) References Cited

PUBLICATIONS

Tahir et al. Development and optimization of methotrexate-loaded lipid-polymer hybrid nanoparticles for controlled drug delivery applications. International Journal of Pharmaceutics, 533(1), 156-168. https://doi.org/10.1016/j.ijpharm.2017.09.061 (Year: 2017).*
Fresenius Kabi USA LLC. Methotrexate Injection, USP. Dailymed. nlm.nih.gov. https://dailymed.nlm.nih.gov/dailymed/fda/fdaDrugXsl.cfm?setid=b585f621-f6c9-4735-ab61-bd1b401f3df0&type=display (Year: 2021).*
Laszlo, J., Humphreys, S. R., & Goldin, A. Effects of Glucose Analogues (2-Deoxy-Dglucose, 2-DeOXY-D-galactose) on Experimental Tumors. Journal of the National Cancer Institute, 24(2), 267-281. (Year: 1960).*
Jiang, R., Jin, B., Danying, W., Zhu, C., Jiang, F., & Gu, L. Therapy Effects of Wogonin on Ovarian Cancer Cells. BioMed Research International, 2017, 1-8. https://doi.org/10.1155/2017/9381513 (Year: 2017).*
Peng, J., Qi, Q., You, Q., Hu, R., Liu, W., Feng, F., Wang, G., & Guo, Q. Subchronic toxicity and plasma pharmacokinetic studies on wogonin, a natural flavonoid, in Beagle dogs. Journal of Ethnopharmacology, 124(2), 257-262. https://doi.org/10.1016/j.jep.2009.04.031 (Year: 2009).*

* cited by examiner

*Primary Examiner* — Yih-Horng Shiao
*Assistant Examiner* — Hoi Yan Lee
(74) *Attorney, Agent, or Firm* — Dogwood Patent and Trademark Law; Ashley D. Johnson

(57) ABSTRACT

The invention is based on the discovery that combination therapy with 2-deoxyglucose, methotrexate, and wogonin provides a synergistic therapeutic effect in selectively killing cancer cells. Advantageously, the disclosed combinatorial therapy does not adversely affect normal, healthy cells. Although the individual compounds have been previously used in cancer treatment, the cited combination has been surprisingly found to selectively kill cancer cells, while not adversely affecting normal, healthy cells, especially those of the immune system. Further, the combination of the compounds produces a synergistic effect, with increased killing of cancer cells compared to each compound alone. Importantly, the combination caused the dying cancer cells to release three key markers of immunogenic cell death: HMGB1, ATP and calreticulin. Immunogenic cell death attracts and activates immune cells against cancers.

13 Claims, 10 Drawing Sheets

COMBINATORIAL THERAPY FOR USE IN INDUCING IMMUNOGENIC CELL DEATH IN CANCER CELLS

CROSS-REFERENCE TO RELATED APPLICATIONS

This application claims priority to U.S. Provisional Patent Application No. 63/286,367, filed Dec. 6, 2021, the entire disclosure of which is hereby incorporated by reference.

TECHNICAL FIELD

The presently disclosed subject matter is generally directed to a combinational therapy for use in inducing immunogenic cell death in cancer cells.

BACKGROUND

The term "cancer" generally refers to any of a group of more than 100 diseases caused by the uncontrolled growth of abnormal cells. Cancer is a widespread problem, with 1.8 million cases diagnosed annually in the United States alone (2020, American Cancer Society). As such, finding compositions and methods for the treatment of cancer is of vital interest. Chemotherapy and radiation therapy are the standard of care for most cancers. However, these treatments are based on targeting proliferating cells rather than only cancer cells, which can produce lethal side effects. In response, targeted therapies for treating cancer are being developed. Specifically, cancer-specific changes of molecules and signaling pathways can be targeted to induce cancer cell death while limiting the detrimental effects on normal cells. For example, monoclonal antibodies used as checkpoint inhibitors can provide anti-cancer treatments. However, the success rate of targeted cancer treatments has shown to be limited. Particularly, induction of cancer cell resistance mechanisms and toxicity to healthy tissues have been observed, especially immune cells. The noted adverse side effects can result in recurrent cancer growth progression, metastasis, bone marrow suppression, and/or patient death. It would therefore be beneficial to provide a system and method of effectively treating cancer that overcomes the shortcomings of the prior art.

SUMMARY

In some embodiments, the presently disclosed subject matter is directed to a pharmaceutical formulation. The formulation comprises a therapeutically effective amount of 2-deoxyglucose or a pharmaceutically acceptable salt thereof, a therapeutically effective amount of methotrexate or a pharmaceutically acceptable salt thereof, a therapeutically effective amount of wogonin or a pharmaceutically acceptable salt thereof, and a pharmaceutically acceptable carrier.

In some embodiments, the therapeutically effective amount of 2-deoxyglucose is about 1-1000 mg/kg patient weight.

In some embodiments, the therapeutically effective amount of methotrexate is about 0.5-5 mg/kg patient weight.

In some embodiments, the therapeutically effective amount of wogonin is about 30-100 mg/kg patient weight.

In some embodiments, the formulation comprises at least one nanoparticle delivery vehicle comprising 2-deoxyglucose, methotrexate, wogonin, or combinations thereof. In some embodiments, the nanoparticle delivery vehicles are selected from polymeric nanoparticles, metallic nanoparticles, liposomes, micelles, and solid lipid nanoparticles.

In some embodiments, the formulation is a slow-release formulation.

In some embodiments, the carrier is selected from lactose, starch, glucose, methyl cellulose, magnesium stearate, mannitol, sorbitol, water, glycerol, buffer, ethanol, or combinations thereof.

In some embodiments, the formulation is configured as a cream, solid, liquid, powder, paste, gel, tablet, granule, foam, pack, ointment, aerosol, solvent, capsule, pill, drink, liposome, syrup, solution, suppository, emulsion, suspension, dispersion, food, beverage, bolus, electuary, paste, or other bio-delivery system or agent.

In some embodiments, the formulation further comprises one or more preservatives, buffers, stabilizers, emulsifiers, antibacterial agents, antifungal agents, wetting agents, colorings, or flavorings, each in an amount of about 0.001-5 weight percent of the formulation.

In some embodiments, the presently disclosed subject matter is directed to a method of treating cancer in a patient in need thereof. The method comprises administering an effective amount of the pharmaceutical formulation to the patient, wherein the pharmaceutical formulation treats the cancer in the patient and does not adversely affect normal, healthy cells.

In some embodiments, the presently disclosed subject matter is directed to a method of killing cancer cells in a patient. The method comprises administering an effective amount of the pharmaceutical formulation to the patient, wherein the pharmaceutical formulation treats the cancer cells in the patient and does not adversely affect normal, healthy cells.

In some embodiments, the patient is a human.

In some embodiments, the therapeutically effective amounts of 2-deoxyglucose, methotrexate, and wogonin exhibit a synergistic effect to treat the cancer or kill the cancer cells.

In some embodiments, the cancer is selected from colon, ovary, skin, kidney, pancreas, and lymphatic organs, cervix, liver, brain, leukemia, or combinations thereof.

In some embodiments, the method further comprises administering one or more additional chemotherapy drugs, radiation, or both to the patient.

In some embodiments, administration of the formulation to the patient is oral administration.

In some embodiments, administration of the formulation to the patent is rectal, nasal, vaginal, subcutaneous, intramuscular, intravenous, intratumor, intraperitoneal, intramammary, intraosseous infusion, transmucosal, transdermal, epicutaneous, intracutaneous, epidural, intrathecal, inhalation, or ophthalmic administration.

In some embodiments, the treatment reduces the severity of one or more symptoms associated with the cancer by at least about 10%, 20%, 30%, 40%, 50%, 60%, 70%, 80%, 90%, 95% or 100% compared to the corresponding symptom in the same subject prior to treatment or compared to the corresponding symptom in other subjects not receiving the treatment.

In some embodiments, the treatment percentage tumor growth inhibition is about 10%, 20, 30%, 40%, 50%, 60%, 70%, 80%, 90%, 95%, or more.

In some embodiments, the method further includes treatment with surgery, radiation therapy, or the use of chemotherapy drugs.

In some embodiments, the presently disclosed subject matter is directed to a kit. The kit comprises the disclosed pharmaceutical formulation and instructions for use thereof for the treatment of cancer.

In some embodiments, the kit can include at least one nanoparticle delivery vehicle comprising 2-deoxyglucose, methotrexate, wogonin, or combinations thereof.

DETAILED DESCRIPTION

Figure 1:
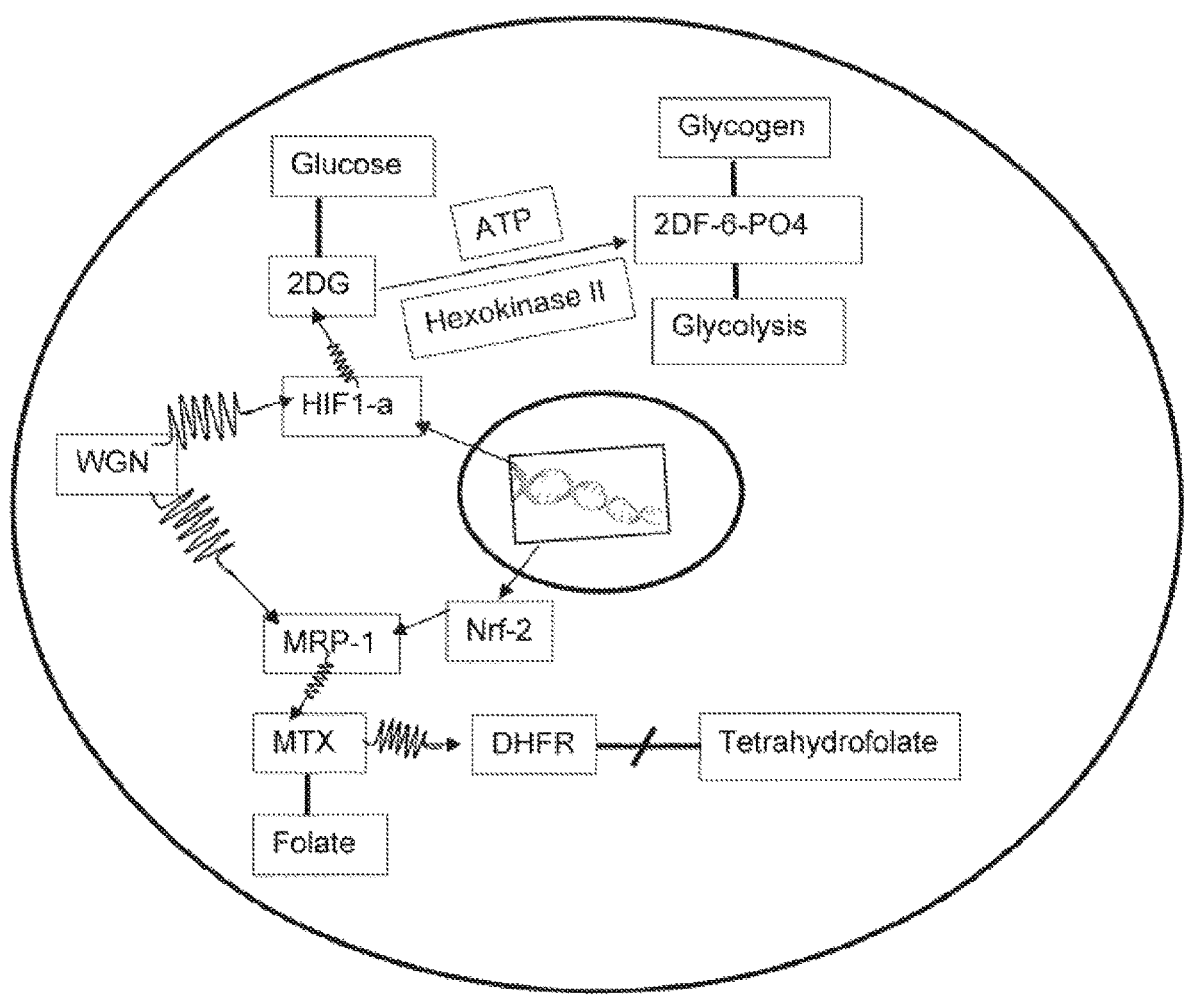
FIG. 1 is a schematic illustrating the synergistic effect of WGN, MTX, and 2-DG on a cancer cell.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

As used herein, the term "and/or" includes any and all combinations of one or more of the associated listed items.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

The presently disclosed subject matter is based on the discovery that combination therapy with 2-deoxyglucose, methotrexate, and wogonin provides a synergistic therapeutic effect in selectively killing cancer cells. The term "combination therapy" refers to the administration of two or more therapeutic substances in conjunction with each other. Advantageously, the disclosed combinatorial therapy does not adversely affect normal, healthy cells. The formulation comprises the three compounds 2-deoxyglucose, methotrexate, and wogonin. Although the individual compounds have been previously used in cancer treatment, the cited combination of compounds has been surprisingly found to selectively kill cancer cells, while not adversely affecting normal, healthy cells. Further, the combination of the compounds produces a synergistic effect, with increased killing of cancer cells compared to each compound alone.

2-deoxyglucose (2-DG) is a compound that targets the glycolytic pathway (Warburg O. Versuche an uberlebendem carcinomgewebe. *Klin. Wochenschr.* 1923; 2:776-777). Specifically, 2-DG is a glucose molecule with the formula $C_6H_{12}O_5$ that has the 2-hydoxyl group replaced by hydrogen, as shown by formula (I) below:

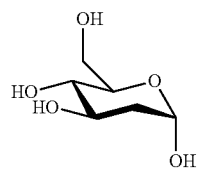

(I)

Because the 2-hydroxyl has been replaced by hydrogen, the 2-DG compound cannot undergo further glycolysis (the metabolic pathway that converts glucose into pyruvic acid). As a result, 2-DG acts to competitively inhibit the production of glucose-6-phosphate from glucose. Cancer cells depend more than normal cells on the consumption of glucose because they shift to using hexokinase II (Xi H., Kurtoglu M., Liu H., Wangpaichitr M., You M., Liu X., Savaraj N., Lampidis T. J., 2-Deoxy-d-glucose activates autophagy via endoplasmic reticulum stress rather than ATP depletion, *Cancer Chemother. Pharmacol.* 2011;67:899-910; Pajak B., Siwiak E., Soltyka M. et al., 2-Deoxy-d-Glucose and Its Analogs: From Diagnostic to Therapeutic Agents, 2-Deoxy-d-Glucose and Its Analogs: From Diagnostic to Therapeutic Agents). Thus, because tumor cells have a higher glucose uptake, they also have a higher uptake of 2-DG, hampering cell growth. As a result, 2-DG inhibits the high rate of glucose metabolism in cancer cells. 2-DG also targets cancer development by inhibiting angiogenesis (the formation of new blood vessels from pre-existing vessels) and by interfering with N-glycosylation (Merchan J. R., Kovács K., Railsback J. W., et al., Antiangiogenic activity of 2-deoxy-D-glucose, *PLoS One,* 2010;5(10); Kurtoglu M., Gao N., Shang J., et al., Under normoxia, 2-deoxy-D-glucose elicits cell death in select tumor types not by inhibition of glycolysis but by interfering with N-linked glycosylation, *Mol Cancer Ther.* 2007;6(11):3049-3058).

When 2-DG is used alone, the compound is rendered inefficient in the presence of hypoxia at the site of a tumor, resulting from HIF-1 alpha up-regulation (Maher J. C., Wangpaichitr M., Savaraj N., Kurtoglu M., Lampidis T. J., Hypoxia-inducible factor-1 confers resistance to the glycolytic inhibitor 2-deoxy-D-glucose, *Mol Cancer Ther.* 2007; 6(2):732-741). HIF-1 alpha is a transcription factor that cancer cells produce in conditions of hypoxia (Zhong H., De Marzo A. M., Laughner E., et al., Overexpression of hypoxia-inducible factor 1α in common human cancers and their metastases, *Cancer Res.* 1999; Eales K. L., Hollinshead K. E. R., Tennant D. A., Hypoxia and metabolic adaptation of cancer cells, *Oncogenesis,* 2016). Additionally, when used alone, the half-life of 2-DG is short and must be used in high concentrations (>5 mM) to be effective (I. L. Hansen, M. M. Levy, D. S. Kerr, The 2-deoxyglucose test as a supplement to fasting for detection of childhood hypoglycemia, Pediatr Res1984 April;18(4):359-64). Adverse effects of 2-DG administration have been shown to occur at doses above 63 mg/kg (Singh D., Banerji A. K., Dwarakanath B. S., Tripathi R. P., et al., Optimizing cancer radiotherapy with 2-deoxy-d-glucose dose escalation studies in patients with glioblastoma multiforme, Onkol. 2005 August; 181(8):507-14).

Methotrexate (MTX) is a widely used chemotherapy agent and immune system suppressant with the formula $C_{20}H22N_8O_5$, shown below as formula (II):

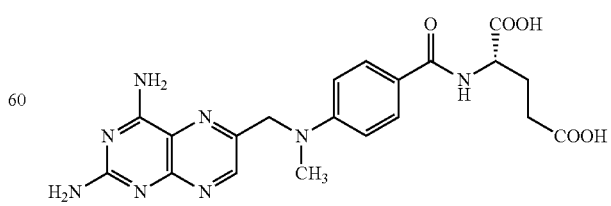

(II)

MTX targets cells that are undergoing proliferation by inhibiting dihydrofolate reductase (DHFR), the enzyme responsible for the synthesis of folic acid (Rajagopalan P. T. R., Zhang Z., McCourt L., et al., Interaction of dihydrofolate reductase with methotrexate: ensemble and single-molecule kinetics, *Proc Natl Acad Sci U S A*. 2002;99(21):13481-13486; Goodsell D. S., The molecular perspective: Methotrexate, *Stem Cells*, 1999;17(5):314-315; Tian H., Cronstein B. N., Understanding the mechanisms of action of methotrexate: Implications for the treatment of rheumatoid arthritis, *Bull NYU Hosp Jt Dis*. 2007;65(3):168-173). Folic acid is a co-factor needed to produce DNA building blocks and is therefore crucial for rapidly dividing cells. The affinity of methotrexate for DHFR is about 1000-fold that of folate. DHFR catalyzes the conversion of dihydrofolate to the active tetrahydrofolate. Folic acid is needed for the de novo synthesis of the nucleoside thymidine, required for DNA synthesis. Also, folate is essential for purine and pyrimidine base biosynthesis, so synthesis will be inhibited. MTX, therefore, inhibits the synthesis of DNA, RNA, thymidylates, and proteins.

When used alone or in combination with other drugs, MTX has not been highly effective at killing cancer cells and/or causes adverse effects. Particularly, when used alone, a decrease in the uptake of the drug has been observed. In addition, a decrease in the retention of the drug due to defective polyglutamylation or an increase in polyglutamate breakdown has been shown. Further, an increase in the DHFR enzyme activity and decrease in the binding of methotrexate to DHFR have been observed (D. Banerjee, E. Ercikan-Abali, M. Waltham, et al., Molecular mechanisms of resistance to antifolates, a review, Acta Biochim Pol1995; 42(4):457-64; Chorawala M., Oza P., Shah G., Mechanisms of anticancer drugs resistance: an overview, *Int J Pharm Sci Drug Res*. 2012; Yu C. P., Hsieh Y. C., Shia C. S., et al., Increased Systemic Exposure of Methotrexate by a Polyphenol-Rich Herb via Modulation on Efflux Transporters Multidrug Resistance-Associated Protein 2 and Breast Cancer Resistance Protein, *J Pharm Sci*. 2016; 105(1):343-349).

Wogonin (WGN) is an O-methylated flavone that is not toxic towards healthy cells, but possesses anti-proliferative, anti-thrombotic, anti-inflammatory, and anti-viral properties (Hui K. M., Huen M. S. Y., Wang H. Y., et al., Anxiolytic effect of wogonin, a benzodiazepine receptor ligand isolated from *Scutellaria baicalensis* Georgi; Huang H. C., Hsieh L. M., Chen H. W, Lin Y. S., Chen J. S., Effects of baicalein and esculetin on transduction signals and growth factors expression in T-lymphoid leukemia cells, *Eur J Pharmacol Mol Pharmacol*. 1994. doi: 10.1016/0922-4106(94); Chen Y. C., Shen S. C., Lee W. R., et al., Wogonin and fisetin induction of apoptosis through activation of caspase 3 cascade and alternative expression of p21 protein in hepatocellular carcinoma cells SK-HEP-1, *Arch Toxicol*. 2002). WGN is found in *Scutellaria baicalensis*, and has the formula $C_{16}H_{12}O_5$ as shown in formula (III):

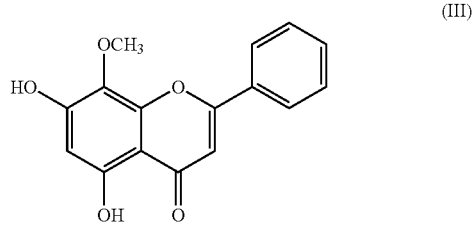 [SMILES: COc1c(O)cc(O)c2c(=O)cc(-c3ccccc3)oc12]

(III)

WGN has been shown to induce apoptosis and endoplasmic reticulum stress in cancer cells (Chengjun Hu, Maozhong Xu, Rujuan Qin, et al., Wogonin induces apoptosis and endoplasmic reticulum stress in HL-60 leukemia cells through inhibition of the PI3K-AKT signaling pathway, Oncol Rep 2015 June;33(6):3146-54). Moreover, the compound can target cancers by inhibiting angiogenesis (the creation of blood vessels necessary to irrigate the fast-growing cancers) (Lin C. M., Chang H., Chen Y. H., Wu I. H., Chiu J. H., Wogonin inhibits IL-6-induced angiogenesis via down-regulation of VEGF and VEGFR-1, not VEGFR-2, *Planta Med*. 2006. doi:10.1055/s-2006-951692; Song X., Yao J., Wang F., et al., Wogonin inhibits tumor angiogenesis via degradation of HIF-1α protein, *Toxicol Appl Pharmacol*. 2013;271(2):144-155). Inflammation induced thrombosis, via NET formation by activated neutrophils is a particularly alarming and dangerous condition many cancer patients suffer, leading to life threatening thrombotic and ischemic events. Thus, the anti-inflammatory role of WGN is beneficial (Sarita Rawat, Gaurav Gupta, Sachchidanand Pathak, et al., Current biological and pharmacological updates on wogonin, EXCLI J. 2020; 19: 635-640).

FIG. 1 is a schematic illustrating the synergistic effects of MTX, 2-DG, and WGN on the metabolic pathways of a cancer cell. As shown, MTX competitively inhibits DHFR, an enzyme that participates in the synthesis of tetrahydrofolate. Folic acid is needed for the synthesis of thymidine, required for DNA synthesis. 2-DG competitively inhibits the production glucose-6-phosphate from glucose (e.g., 2-DG acts as a glycolysis inhibitor). Further, WGN possesses anti-inflammatory properties, and can induce apoptosis in cancer cells. The combinatorial pathway targets three critical cancer survival pathways: DNA synthesis, metabolism, and immune evasion.

The compounds used in the disclosed formulation can be administered alone but will generally be administered as a single pharmaceutical formulation (e.g., the components are in admixture with a suitable pharmaceutical excipient, diluent or carrier selected with regard to the intended route of administration and standard pharmaceutical practice).

Figure 2A:
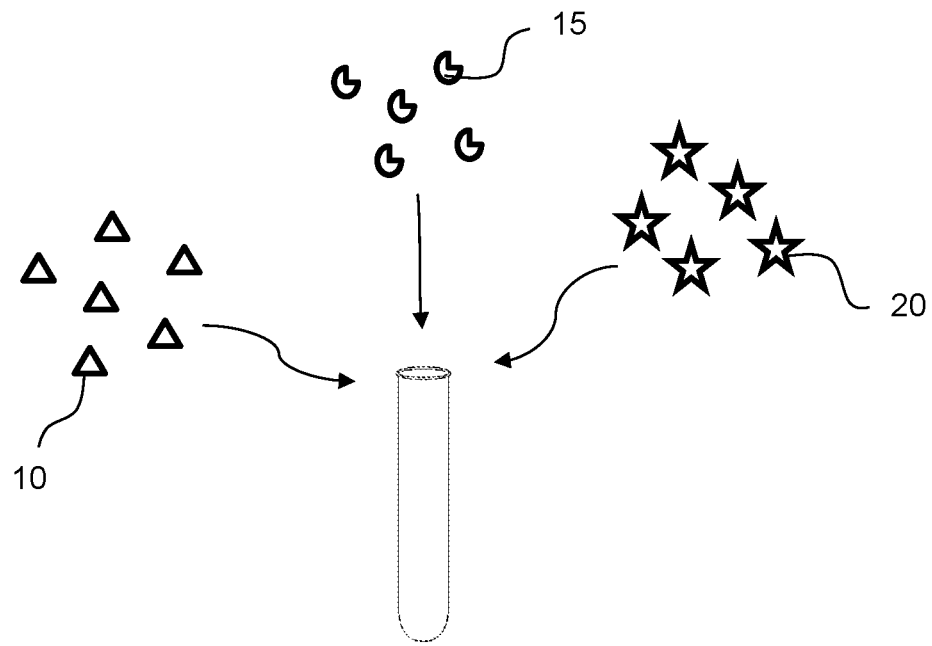
FIGS. 2a and 2b are schematics illustrating the combination of WGN, MTX, and 2-DG into a formulation.
Figure 2B:
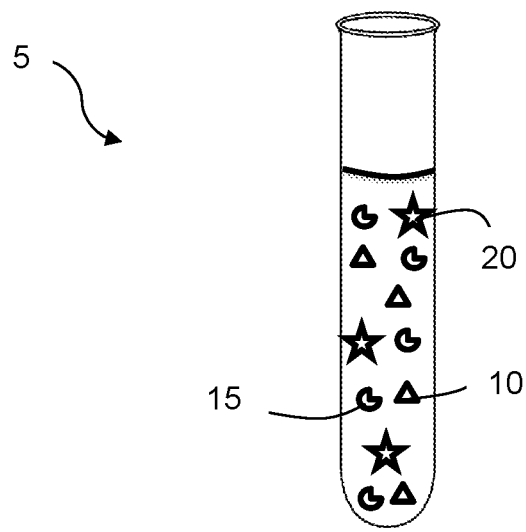

As shown in FIGS. 2a and 2b, formulation 5 comprises therapeutically effective amounts of 2-DG 10, MTX 15, and WGN 20 that are together administered to a patient. The term "therapeutically effective amount" is defined as an amount of one or more of the active ingredients, administered to an animal or human at a dose such that efficacy of the treatment can bring about remission, prevention, or halting of tumor growth or any other desired clinical result. The formulation may be presented in unit dosage form and may be prepared by any method well known in the art of pharmacy.

In some embodiments, a therapeutically effective amount of 2-DG is about 1-1000 mg/kg patient weight. Thus, the formulation can comprise at least about (or no more than about) 1, 10, 50, 100, 150, 200, 250, 300, 350, 400, 450, 500, 550, 600, 650, 700, 750, 800, 850, 900, 950, or 1000 mg 2-DG per kg body weight. The therapeutically effective amount of MTX present in a single dose of formulation 5 can be about 0.5-5 mg/kg patient weight. Thus, the formulation can comprise at least about (or no more than about) 0.5, 1, 1.5, 2, 2.5, 3, 3.5, 4, 4.5, or 5 mg/kg body weight. For WGN, a therapeutically effective amount comprises about 30-100 mg/kg patient body weight. Accordingly, the formulation can comprise at least about (or no more than about) 30, 35, 40, 45, 50, 55, 60, 65, 70, 75, 80, 85, 90, 95, or 100 mg/kg patient body weight.

The disclosed components can be formulated into a pharmaceutical formulation, such as by mixing with a suitable carrier and/or diluent using techniques that are known in the art. The term "carrier" refers to a compound that facilitates the incorporation of a compound into cells or tissues. Examples of suitable carriers include (but are not limited to) lactose, starch, glucose, methyl cellulose, magnesium stearate, mannitol, sorbitol, and the like. The term "diluent" refers to a reagent used for dilution or dissolution, such as (but not limited to) water, glycerol, buffer, and/or ethanol. Acceptable carriers or diluents for therapeutic use are well known in the pharmaceutical art, as described in Remington's Pharmaceutical Sciences, Mack Publishing Co. (A. R. Gennaro edit. 1985), incorporated herein by reference. The choice of pharmaceutical carrier and/or diluent can be selected with regard to the intended route of administration and standard pharmaceutical practice.

The form of a pharmaceutically acceptable carrier used to deliver the treatment to a patient can be selected from a cream, solid, liquid, powder, paste, gel, tablet, granule, foam, pack, ointment, aerosol, solvent, capsule, pill, drink, liposome, syrup, solution, suppository, emulsion, suspension, dispersion, food, bolus, electuary, paste, or other bio-delivery system or agent. The disclosed formulation therefore includes pharmaceutically acceptable carriers and delivery systems adapted for varying routes of administration such as oral, rectal, nasal, vaginal, subcutaneous, intramuscular, intravenous, intratumor, intraperitoneal, intramammary, intraosseous infusion, transmucosal, transdermal, epicutaneous, intracutaneous, epidural, intrathecal, inhalation, ophthalmic, or any other suitable route.

Thus, formulation 5 can be adapted for oral administration, taking the form of liquids, syrups, beverages, capsules, powders, granules, solutions, suspensions, tablets, food, lozenges, or any other form in which the active ingredients are taken by mouth and absorbed through the alimentary canal. However, it should be appreciated that formulation 5 is not limited to oral administration.

As a general principle, suitable carriers and diluents do not react with the active components of the disclosed formulation in a manner that substantially degrades or otherwise adversely affects WGN, 2-DG, and/or MTX. Further, the carrier and/or diluent should be suitable for administration into a subject along with the active compounds.

Optionally, formulation 5 can include one or more additives, such as (but not limited to) preservatives, buffers, stabilizers, emulsifiers, antibacterial agents, antifungal agents, wetting agents, colorings, flavorings, and the like. In some embodiments, the additives can be present in an amount of about 0.001-5 weight percent of the formulation. These materials are well known in the art.

Formulation 5 can be prepared in bulk or in unit dosage form. The unit dosage form can include any of a variety of forms, such as (but not limited to) a capsule, a liquid, an IV bag, a tablet, a single pump on an aerosol inhaler, or a vial. The quantity of active ingredient in the formulation in a unit dose of composition is an effective amount and is varied according to the particular treatment involved. The disclosed composition comprises therapeutic amounts of 2-DG, MTX, and WGN administered to a patient (e.g., orally) that will suffice to elicit death in cancer cells and cause them to release substances that alert and activate the immune system via immunogenic cell death. One skilled in the art will appreciate that it may be necessary to make routine variations to the dosage depending on the age, size, and/or condition of the patient. The dosage will also depend on the route of administration.

In some embodiments, formulation 5 can be in slow-release form. Those of skill in the art will appreciate that the frequency of dosing of a slow-release form will be different from the dosing frequency described herein for non-slow-release formulations and dependent on the pharmacokinetics of the particular slow-release form employed.

Slow-release formulations deliver effective doses of MTX, 2-DG, and WGN with a delay after administration (e.g., delayed-release dosage) or fora prolonged period of time (extended release). Thus, in some embodiments, the formulation is designed to release the active compounds a predetermined time after administration to the patient (e.g., 0.5, 1, 1.5, 2, 3 or more hours after administration). In other embodiments, the release of the compounds is sustained over a predetermined period of time (at a constant or non-constant rate).

Any method of providing slow-release characteristics to formulation 5 can be used. For example, the active compounds can be incorporated in a water insoluble binder that will disperse very slowly after administration to the patient. Alternatively, the formulation can include an insoluble or biodegradable matrix that binds the active compounds. Further, capsules, pills, and tablets can be configured with exterior coatings to slow dispersion. Any method of providing slow-release characteristics to formulation 5 can be used.

In some embodiments, formulation 5 can include nanoparticles or microparticles comprising MTX, 2-DG, and WGN. The term "nanoparticle" refers to a particle of matter with a diameter of between about 1-100 nanometers in diameter. The term "microparticle" refers to particles with a diameter of between about 1-1000 um in size.

In some embodiments, formulation 5 can form part of a kit. Specifically, the kit can include the disclosed formulation and instructions for use. For example, the kit can include a dried or concentrated amounts of MTX, 2-DG, and WGN and a container housing various carriers, buffers, reagents, and other standard ingredients well known in the art. Containers and/or kits can include labeling with instructions for use and/or warnings.

In use, formulation 5 can be administered to a patient in need of treatment. As set forth in detail herein above, the disclosed formulation comprises therapeutically effective amounts of MTX, 2-DG, and WGN that provide a synergistic effect in the treatment of cancer in the patient.

The term "patient" as used herein can refer to a human. However, the presently disclosed subject matter is not limited and the disclosed formulation can be used for veterinary purposes in the treatment of cancer in an animal (e.g., dogs, cats, rabbits, cows, horses, pigs, goats, ponies, chickens, fish, lizards, birds, and the like).

As used herein, "treatment" or "treating" is an approach for obtaining beneficial or desired results including clinical results. Thus, beneficial or desired clinical results can include (but are not limited to) one or more of the following: alleviating one or more symptoms of cancer, diminishing the extent of the cancer, stabilizing cancer (e.g., preventing or delaying the worsening of the cancer), preventing or delaying the spread (e.g., metastasis) of the cancer, preventing or delaying the recurrence of the cancer, reducing recurrence rate of the cancer, delay or slowing the progression of the cancer, providing a remission (partial or total) of the cancer, decreasing the dose of one or more other medications required to treat the cancer, delaying the progression of the cancer, increasing the quality of life, and/or prolonging survival. In some embodiments, the treatment reduces the severity of one or more symptoms associated with cancer by at least about any of 10%, 20%, 30%, 40%, 50%, 60%, 70%, 80%, 90%, 95% or 100% compared to the corresponding symptom in the same subject prior to treatment or compared to the corresponding symptom in other subjects not receiving the treatment. Also encompassed by "treatment" is a reduction of pathological consequence of cancer. The methods of the invention contemplate any one or more of these aspects of treatment.

A variety of administration routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of the formulation include powders, sprays, ointments, pastes, creams, lotions, gels, solutions, patches, and inhalants.

For example, the formulation can be orally administered with an inert diluent, with an assimilable edible carrier, enclosed in hard or soft shell gelatin capsules, compressed into tablets, suspended in a liquid or gel, and/or incorporated directly with the food of the diet. The tablets, pills, capsules, and the like can optionally include a binder such as gum tragacanth, acacia, corn starch, or gelatin; excipients such as dicalcium phosphate; a disintegrating agent such as corn starch, potato starch, alginic acid, and the like; a lubricant such as magnesium stearate; a sweetening agent such as saccharin; and/or a flavoring agent such as peppermint, oil of wintergreen, or cherry flavoring. In addition, the active compound can be incorporated into sustained-release preparations and formulations, as discussed above.

For parenteral injection (e.g., intravenous, intramuscular, subcutaneous, intraperitoneal, intratumoral), the active components MTX, 2-DG, and WGN can be dissolved or suspended in a sterile solution suitable for injection. For parenteral administration, the formulations can include one or more pharmaceutically acceptable ingredients, such as a tonicity agent (including but not limited to NaCl, mannitol, and the like), an antioxidant (including but not limited to sodium bisulfite, sodium metabisulfite, ascorbic acid, and the like), and/or a preservative (including but not limited to benzyl alcohol, methyl paraben, propyl paraben, a combination of methyl and propyl parabens, and the like).

The pharmaceutical forms suitable for injectable use include sterile aqueous solutions or dispersions and sterile powders for the extemporaneous preparation of sterile injectable solutions or dispersions. In all cases, the form should be sterile and, in final form, must be fluid to the extent that easy syringability exists. It should further be stable under the conditions of manufacture and storage and must be preserved against the contaminating action of microorganisms such as bacteria and fungi.

In some embodiments, the disclosed formulation can be administered topically, e.g., using a transdermal patch. The pharmaceutical forms suitable for topical use include oil and water emulsions and liposomal formulations, as well as lotions, creams, and ointments commonly used for topical administration of drugs. The carrier can be a solvent or dispersion medium containing, for example, water, ethanol, polyol, for example, glycerol, propylene glycol, and liquid polyethylene glycol, and the like, suitable mixtures thereof, and vegetable oils.

As is understood in the art, an "effective amount" may be in one or more doses, i.e., a single dose or multiple doses may be required to achieve the desired treatment endpoint. An effective amount may be considered in the context of administering one or more therapeutic agents. The components in the combination therapy can be administered sequentially, simultaneously, or concurrently using the same or different routes of administration for each component. Thus, an effective amount of a combination therapy includes an amount 2-DG, MTX, and WGN that when administered sequentially, simultaneously, or concurrently produces a desired outcome.

Formulation 5 can be used to treat any cancer. For example, the disclosed formulations and methods can be used to treat malignancy of any type including, cancer of the lung, breast, testes, prostate, colon, ovary, skin, kidney, pancreas, lymphatic organs, cervix, liver, brain, and leukemia.

Typically, a physician will determine the actual dosage that will be most suitable for an individual patient. The specific dose level and frequency of dosage for any particular patient can be varied and will depend upon a variety of factors including the nature of the cancer, the therapy sought, the severity of the disease, the degree of malignancy, the extent of metastatic spread, the tumor load, general health status, body weight, age, sex, and genetic background of the patient. Accordingly, the therapeutically effective amount of each component of formulation 5 can vary and is ultimately at the discretion of the medical practitioner.

During treatment of a patient, formulation 5 can be delivered over a treatment cycle. The treatment cycle can be any suitable length of time. For example, formulation 5 can be administered to a patient once per day, every other day, every third day, or once per week. The formulation can be administered for a desired amount of time, such as at least two, three, four, five, or at least six weeks within a twelve-month period. However, it should be appreciated that the treatment cycle of formulation 5 is not limited and can vary based on the particular type of cancer, progression of cancer, age/weight of patient, and the like.

Consistent with administration regimens of other anticancer agents, formulation 5 can be administered in multiple "rounds" of administration. For example, in some embodiments, the formulation can be administered once daily for at least 3-10 or 5-10 consecutive days, repeated once, twice, or three or more times. Optionally, the treatment period can include one or more no-treatment periods ranging from about one to several weeks between each treatment.

Cancer treatments can be evaluated by tumor regression, tumor weight or size shrinkage, time to progression, duration of survival, progression free survival, overall response rate, duration of response, quality of life, protein expression, and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation $100-(T/C\times100)$, where T is the mean relative tumor volume of the treated tumor, and C is the mean relative tumor volume of a non-treated tumor. In some embodiments, the % TGI using formulation 5 is about 10%, about 20%, about 30%, about 40%, about 50%, about 60%, about 70%, about 80%, about 90%, about 91%, about 92%, about 93%, about 94%, about 95%, or more than 95%.

The formulation can be administered alone or in combination to augment any chemotherapy agent(s) including but not limited to: acetogenins, actinomycin D, adriamycin, aminoglutethimide, asparaginase, bleomycin, bullatacin, busulfan, carmustine, carboplatin, chlorambucil, cisplatin, cyclophosphamide, cytarabine, dacarbazine, daunorubicin, doxorubicin, epirubicin, estradiol, etoposide, fludarabine, flutamide, fluorouracil, floxuridine, gemcitabine, glaucarubolone, hexamethylmelamine, hydroxyurea, idarubicin, ifosfamide, interferon, irinotecan, leuprolide, lomustine, mechlorethamine, melphalan, mercaptopurine, methotrexate, mitomycin, mitoxantrone, mitotane, oxaliplatin, pentostatin, plicamycin, procarbazine, quassinoids, simalikalactone, steroids, streptozocin, semustine, tamoxifen, taxol, taxotere, teniposide, thioguanine, thiotepa, tomudex, topotecan, treosulfan, vinblastine, vincristine, vindesine and vinorelbine or mixtures thereof.

Furthermore, the disclosed formulation can be used together with other modalities such as immunotherapy and/or radiation.

Using the therapeutically effective dosing and administration regimen, practitioners of skill in the art can significantly improve treatment outcomes achieved with currently used cancer therapies (including surgical resection, radiation therapy, and drug therapies), as well as with new drug therapies in development.

EXAMPLES

The following Examples provide illustrative embodiments. In light of the present disclosure and the general level of skill in the art, those of ordinary skill in the art will appreciate that the following Examples are intended to be exemplary only and that numerous changes, modifications, and alterations can be employed without departing from the scope of the presently disclosed subject matter.

Example 1

Determination of the Effective Dose of 2-DG, MTX, and WG

The 50% effective dose (or $ED_{50}$) for 2-DG, MTX, and WGN (individually) against the cancer cell lines 4T1 (mouse breast cancer), MCF-7 (human breast cancer), THP-1 (human myelomonocytic cancer), and B16-F10 (mouse melanoma) was determined (Table 1). The cell lines were specifically chosen for their extremely aggressive nature. For example, the cell lines have evolved multiple mechanisms of resistance to cell death and are highly metastatic (e.g., equivalent to a stage 4 cancer model). In this assay, a Determination of the ED50 using the MTS cell viability assay Analysis of the effects of MTX-2DG-WGN combination on cell growth was performed with an MTS kit (CellTiter 96® AQueous One Solution Cell Proliferation Assay Kit, Promega, Madison, WI, USA) according to the manufacturer's instruction. 4-T1, MCF-7, B16-F10, and THP-1 cells were seeded into 96-well plates at a density of $10 \times 10^3$ cells per well with three replicates. The cells were treated as indicated (MTX, 2DG, and WGN were added initially at concentrations of 100 μM, 50 mM, and 200 μM, respectively, followed by serial two-fold dilutions) and incubated for 48 hours at 5% $CO_2$ at 37° C. After 48 h, 20 μL of CellTiter 96® AQueous One Solution MTS (5 mg/mL) (Promega—Madison, WI, USA) was added to each well and incubated at 5% $CO_2$ at 37° C. for an additional 4 hours. Absorbance readings were taken in an Epoch microplate reader at 490 nm. Computed data was compared to untreated and normalized cells. Cells that were not administered any treatment were considered the control group. Cell viability was calculated by the following formula: Cell viability (%)=(average OD in treated group/average OD in control group)×100%. A dose-activity curve with the concentration spectrum was prepared.

Determination of $EC_{50}$

The $EC_{50}$ was extrapolated from the dose-response graph. The drug concentration that caused 50% maximum effect with regards to cytotoxicity was determined by plotting triplicate data points over a concentration range and calculating values using regression analysis of GraphPad PRISM v8 program.

Statistical Analysis

GraphPad Prism v8 software was used for statistical analyses. Data is presented as mean±s.d. t-test was used to determine statistical significance between groups for normally distributed data. Linear regression analysis performed by the GraphPad Prism software was used to calculate $r^2$. For all tests, *p<0.05 was considered significant. Experiments and measurements were performed in triplicate. Data depicts means of triplicates±s.e.m. and are representative of three experiments.

TABLE 1

| | ED50 determinations of each individual drug on different cancer cell lines | | | |
|---|---|---|---|---|
| Compound | $ED_{50}$ in 4T1 | $ED_{50}$ in MCF-7 | $ED_{50}$ in THP-1 | $ED_{50}$ in B16-F10 |
| MTG | 0.049 uM | 0.049 uM | 1.82 uM | 0.019 uM |
| 2-DG | 6.25 mM | 19.65 mM | 11.62 mM | 0.35 mM |
| WGN | 85 uM | 20.22 uM | 83 uM | 76 uM |

Example 2

Synergistic Effect of 2-DG, MTX, and WGN on 4T1 and MCF7 Cell Lines

MTX, 2-DG, and WGN were tested alone and in combination. Specifically, each compound was tested at the $ED_{50}$ value, 2× below the $ED_{50}$ value, 4× below the $ED_{50}$ value, and 6× below the $ED_{50}$ value. The combination of all 3 compounds was also tested, along with a negative control (untreated). The results are shown for 4T1 mouse breast cancer cells (FIG. 3a) and MCF7 human breast cancer cells (FIG. 3b).

Figure 3A:
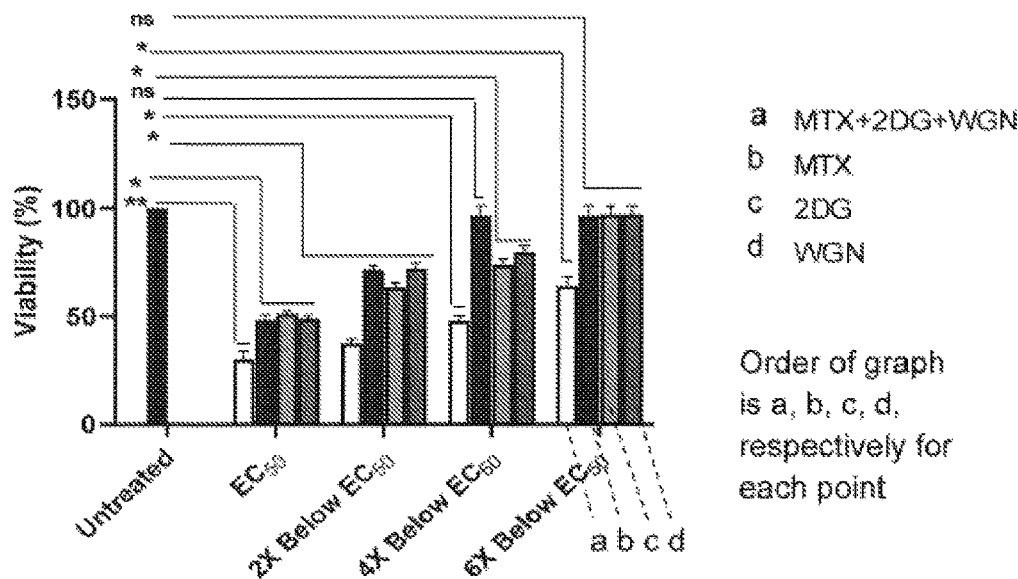
FIG. 3a is a bar graph illustrating the percent viability of 4T1 mouse breast cancer cells when untreated, treated with MTX, 2-DG, WGN, and MTX+2-DG+WGN at ED50, 2× below ED50, 4× below ED50, and 6× below ED50.
Figure 3B:
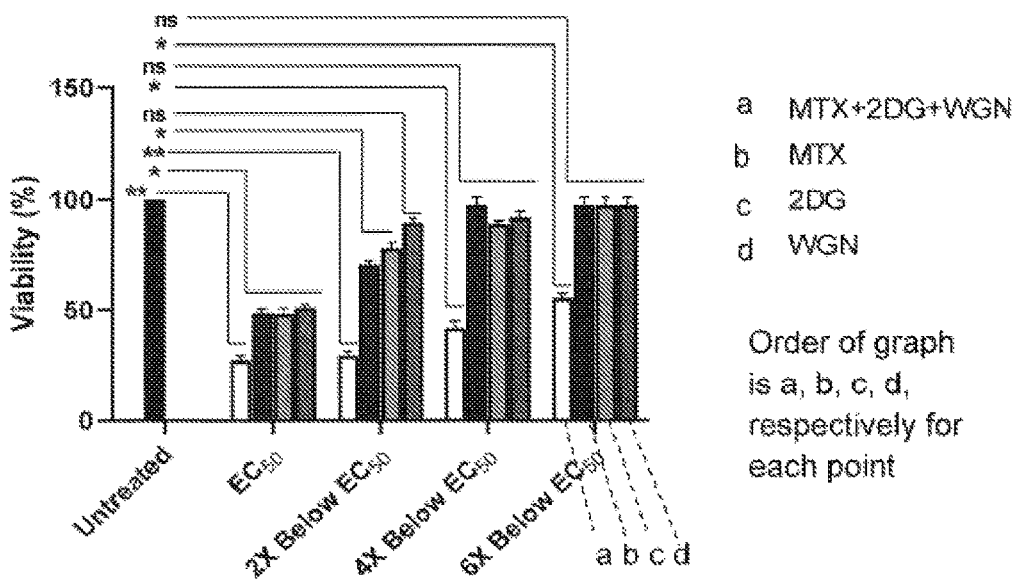
FIG. 3b is a bar graph illustrating the percent viability of MCF7 human breast cancer cells when untreated, treated with MTX, 2-DG, WGN, and MTX+2-DG+WGN at ED50, 2× below ED50, 4× below ED50, and 6× below ED50.

Data indicates that the combination of MTG, 2-DG, and WGN is significantly effective at inhibiting cancer cell growth when used at 2×, 4× and 6× lower concentrations than the ideal $ED_{50}$ for each compound, as shown in FIGS. 3a and 3b. Importantly, the data shows that even when used at a concentration 6× lower than the $ED_{50}$ concentrations, the combination of the MTG, 2-DG, and WGN has over 50% efficacy in killing cancer cells (yellow bar), whereas each compound alone at those concentrations has no effect whatsoever (blue, green, red bars). The synergistic effect was observed at the $ED_{50}$ concentration, 2×, 4×, and 6× lower than their respective $ED_{50}$ values.

The testing protocol was the same as that described for the ED50 noted above.

Example 3

Synergistic Effect of 2-DG, MTX, and WGN on THP-1 and B16-F10 Cell Lines

Figure 4A:
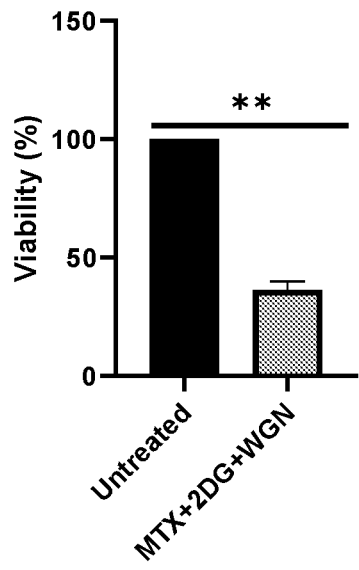
FIG. 4a is a bar graph illustrating percent viability of THP-1 human myelomonocytic cells when untreated versus when treated with the combination of MTX+2-DG+WGN.
Figure 4B:
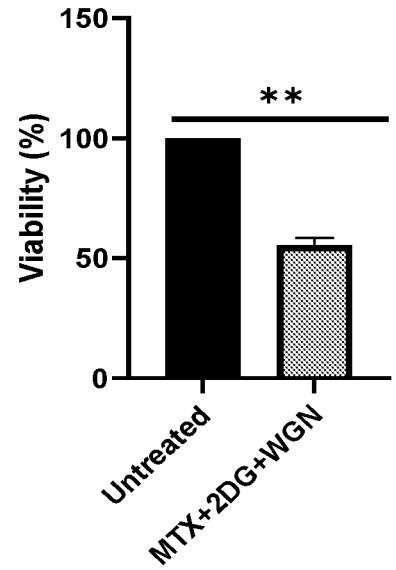
FIG. 4b is a bar graph illustrating percent viability of B16-F10 human melanoma cells when untreated versus when treated with the combination of MTX+2-DG+WGN.

The combination of MTX, 2-DG, and WGN were tested on THP-1 human myelomonocytic cells and B16-F10 human melanoma cells. Specifically, the combination of all 3 compounds were used in combination at concentrations 6× lower than their respective $ED_{50}$, along with a negative control (untreated). The results are shown in THP-1 human myelomonocytic cells (FIG. 4a) and B16-F10 human melanoma cells (FIG. 4b). The figures show the efficacy of the compounds in reducing cell viability.

Determination of Cell Viability Using the MTS Assay

Analysis of the effects of MTX-2DG-WGN combination on cell growth was performed with an MTS kit (CellTiter 96® AQueous One Solution Cell Proliferation Assay Kit, Promega, Madison, WI, USA) according to the manufacturer's instruction. 4-T1, MCF-7, B16-F10, and THP-1 cells were seeded into 96-well plates at a density of $10 \times 10^3$ cells per well with three replicates. The cells were treated as indicated (MTX, 2DG, and WGN were added initially at concentrations of 100 µM, 50 mM, and 200 µM, respectively, followed by serial two-fold dilutions) and incubated for 48 hours at 5% $CO_2$ at 37° C. After 48 h, 20 µL of CellTiter 96® AQueous One Solution MTS (5 mg/mL) (Promega—Madison, WI, USA) was added to each well and incubated at 5% $CO_2$ at 37° C. for an additional 4 hours. Absorbance readings were taken in an Epoch microplate reader at 490 nm. Computed data was compared to untreated and normalized cells. Cells that were not administered any treatment were considered the control group. Cell viability was calculated by the following formula: Cell viability (%)=(average OD in treated group/average OD in control group)×100%.

Example 4

Colony Formation Inhibition Assay

Figure 5A:
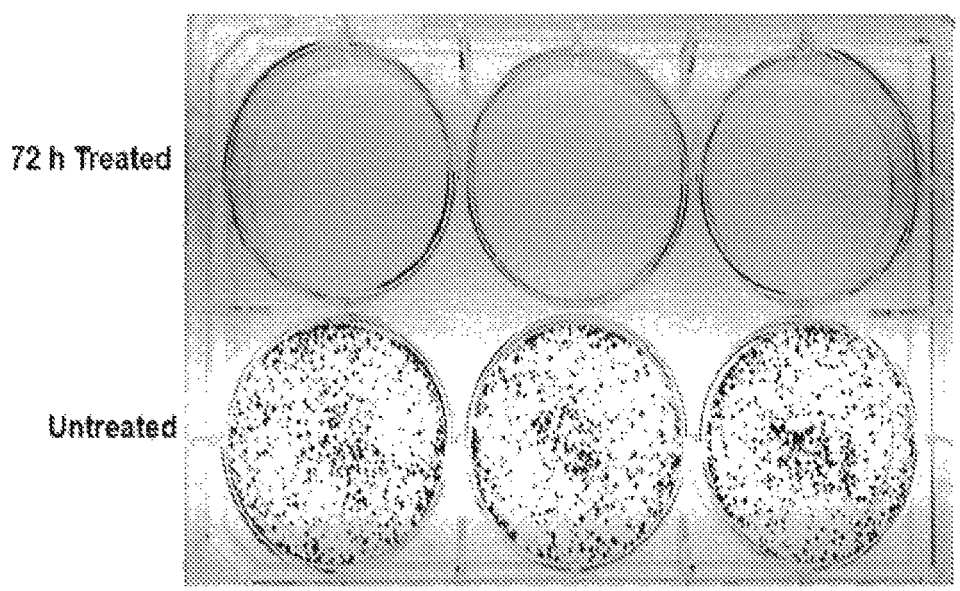
FIG. 5a is a photograph illustrating plates after a colony formation inhabitation assay using 4T1 cancer cells untreated versus treated with the combination of MTX+2-DG+WGN after 72 hours.
Figure 5B:
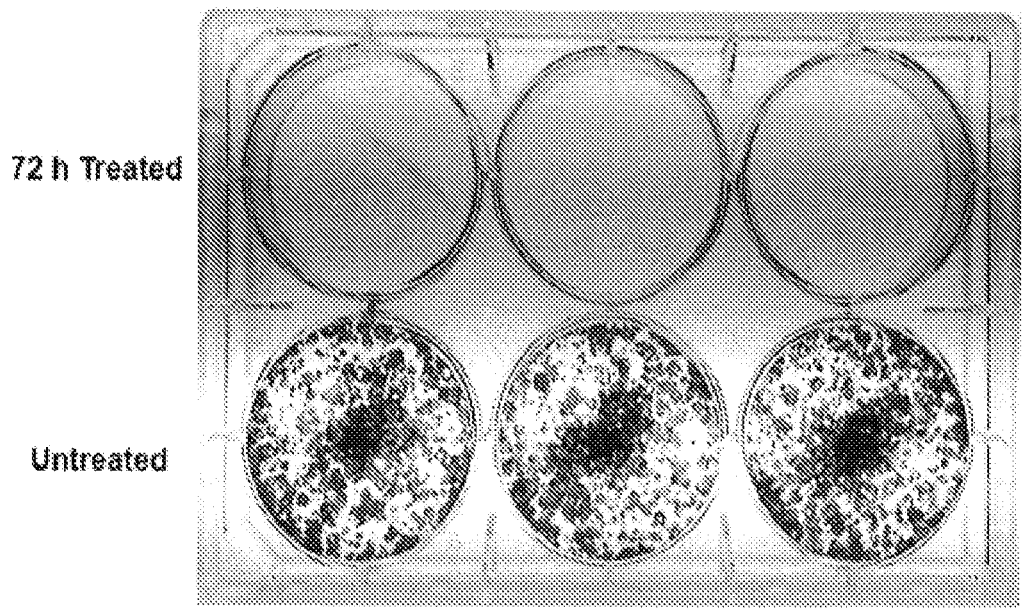
FIG. 5b is a photograph illustrating plates after a colony formation inhabitation assay using MCF-7 cancer cells untreated versus treated with the combination of MTX+2-DG+WGN after 72 hours.

A colony formation inhibition assay was used on the combination of MTX, 2-DG, and WGN. The three drugs combined proved to be highly efficient at inhibiting cancer colonies when cells were treated for up to 72 hours. Drugs were used at 6× lower concentration than their respective $ED_{50}$ dose in 4T1 mouse breast cancer cells (FIG. 5a) and MCF-7 human breast cancer cells (FIG. 5b).

In Vitro Colony-Forming Assay

Freshly isolated 4-T1 or MCF-7 cells were seeded at a clonal density of 500 cells/well onto tissue culture-treated polystyrene 6 well flat bottom plates and cultured in growth medium Gibco RPMI 1640 L-Glutamine (Life Technologies—Grand Island, NY, USA), supplemented with 10% certified heat-inactivated fetal bovine serum (FBS). Careful attention was made to not disturb cells 72 hours after culture to allow adherence. A 50% media change was performed on day 3. After 72 hours, media was changed, and experimental wells were treated with MTX-2DG-WGN drug combination at 6× below their respective ED50. Control wells were left untreated. Colonies were monitored microscopically to ensure they were derived from single cells. Cells were incubated for 72 h at 5% $CO_2$ at 37° C. Cultures were terminated after 72 h and washed free of media with cold PBS. Colonies were fixed with methanol, and stained with 0.5% crystal violet tissue culture stain for count.

Example 5

Comparison of the Activity of MTX+2-DG+WGN and Doxorubicin in Cancer Cells

Figure 6A:
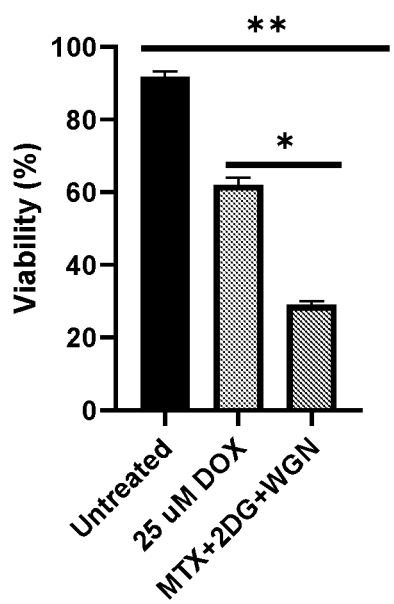
FIG. 6a is a bar graph illustrating the percent viability of 4T1 cancer cells when untreated, treated with 25 uM doxorubicin, and with the combination of MTX+2-DG+WGN.
Figure 6B:
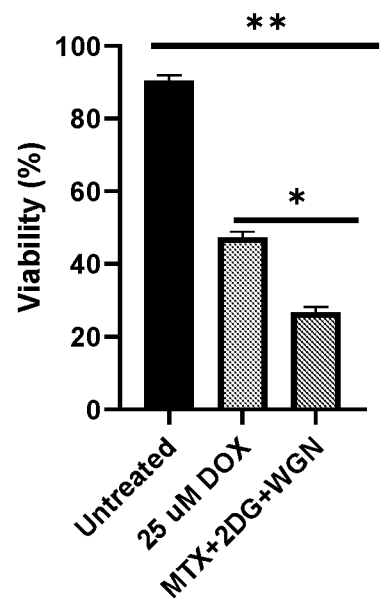
FIG. 6b is a bar graph illustrating the percent viability of MCF-7 cancer cells when untreated, treated with 25 uM doxorubicin, and with the combination of MTX+2-DG+WGN.

Doxorubicin is the chemotherapy drug that is standard of care for treatment of advanced metastatic cancers. It causes severe side effects and cancer cells develop resistance to this drug by upregulating the multidrug resistant pump. The disclosed combinatorial drug treatment was compared using trypan blue dye exclusion with doxorubicin, using it at its use concentration of 25 uM and the combination of drugs at concentrations 6× below their respective $ED_{50}$. Cells were treated for 24 hr in culture using 4T1 mouse breast cancer cells (FIG. 6a) and MCF-7 human breast cancer cells (FIG. 6b).

The data shows that the cancer cells are killed more effectively using the combination of MTX, 2-DG, and WG at 6× lower dose than each compound's respective ED50 compared to doxorubicin used at its standard care concentration of 25 uM.

Example 6

Cancersphere Treatment with MTX+2-DG+WGN

Figure 7A:
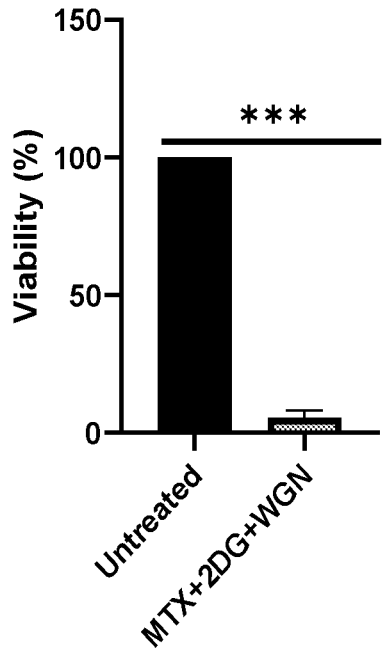
FIG. 7a is a bar graph illustrating percent viability of 4T1 cancer cells untreated versus treated with the combination of MTX+2DF+WGN.
Figure 7B:
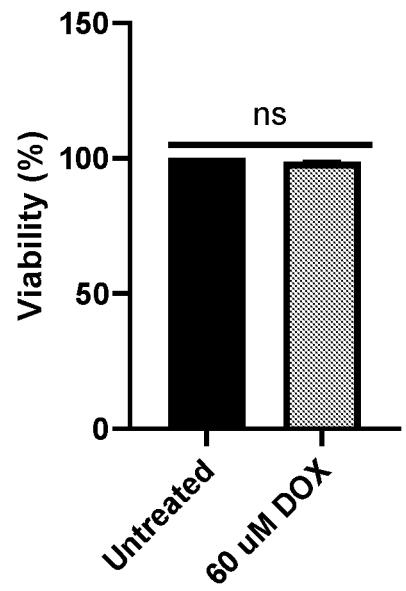
FIG. 7b is a bar graph illustrating percent viability of 4T1 cancer cells untreated versus treated with doxorubicin.
Figure 7C:
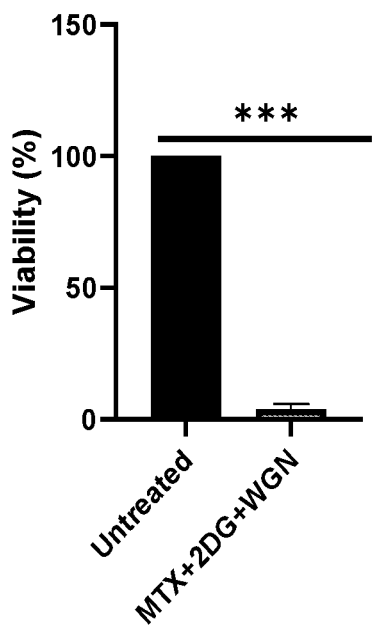
FIG. 7c is a bar graph illustrating percent viability of MCF-7 cancer cells untreated versus treated with the combination of MTX+2DF+WGN.
Figure 7D:
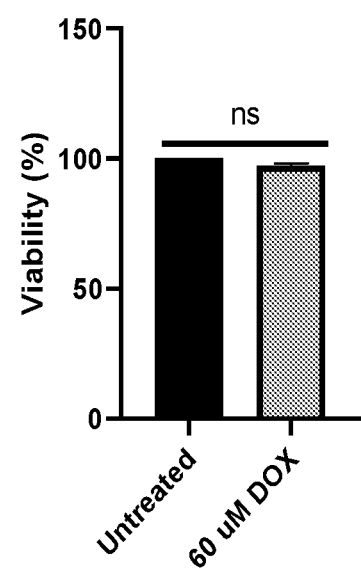
FIG. 7d is a bar graph illustrating percent viability of MCF-7 cancer cells untreated versus treated with doxorubicin.

A new model for tumor growth in vitro has been established as 3D cultures known as cancerspheres. To evaluate the clinical translatability and predictivity of the novel combinatorial therapy in vivo, 3D cancerspheres suspended in media containing extracellular matrix proteins (ECM) were treated with the combination of MTX, 2-DG, and WGN. The results are shown in FIGS. 7a and 7b (4T1 mouse breast cancer cells) and FIGS. 7c and 7d (MCF-7 human breast cancer cells), indicating significant efficacy of the combination against both human and mouse mammary 3D cancer models.

Cell Culturing and Maintenance

The 4-T1 (Mouse Metastatic Mammary Carcinoma) cell line was kindly donated by Dr. Vijaya Iragavarapu-Charyulu, Department of Biomedical Sciences, Florida Atlantic University. The MCF-7 (Human Metastatic Mammary Tumor) cell line was obtained from Dr. James X. Hartmann, Department of Biological Sciences, Florida Atlantic University. Cells were cultured between $2 \times 10^5$/mL and $1 \times 10^6$/mL in 75 $cm^2$ Falcon cell culture flaks containing Gibco RPMI 1640-L-Glutamine medium (Life Technologies—Grand Island, NY, USA) supplemented with 10% fetal bovine serum (Life Technologies—Grand Island, NY, USA) and 100 U/mL Gibco Pen Strep (Life Technologies—Grand Island, NY, USA). Cell cultures were incubated at 37° C. under 5% $CO_2$ in a humidified atmosphere.

3D Tumor Model Culture

Mammary tumorspheres were grown using Matrigel® Extracellular Matrix Basement Membrane (Corning, USA). 4-T1 and MCF-7 cells were cultured independently and harvested in a single-cell suspension with Gibco RPMI 1640-L-Glutamine medium (Life Technologies—Grand Island, NY, USA) supplemented with 10% fetal bovine serum (Life Technologies—Grand Island, NY, USA) and 100 U/mL Gibco Pen Strep (Life Technologies—Grand Island, NY, USA) at a density of $3 \times 10^5$ cells/mL. Matrigel® Extracellular Basement Membrane (Corning, USA) was used to coat the bottom of ultra-low attachment surface 6-well plates (Corning, USA) and incubated for 30 min at 37° C. to gel. Cells suspended in complete medium were then carefully seeded on top of the matrix gel and incubated for an additional 30 min at 37° C. under 5% $CO_2$ in a humidified atmosphere. Complete R-10 media supplemented with 10% Matrigel® Extracellular Basement Membrane was then added to each well. Cell cultures were incubated at 37° C. under 5% $CO_2$ in a humidified atmosphere for 8 days. Media was changed every two days.

Trypan Blue Exclusion Cell Viability Assay

After 8 days of culture and 48 h treatment, tumorspheres of roughly 50 cells or more were selected for qualitative analysis. Trypan blue dye was added to all wells and incubated for 10 min at 37° C. at 5% $CO_2$. After 5 min, tumorspheres were analyzed microscopically. Viable spheroids were characterized as luminescent and unstained. Dead (non-viable) spheroids were characterized as stained and displaying no luminescence.

MTS Cell Viability Assay

On the $8^{th}$ day of culture, media from MCF-7 and 4-T1 mammary tumorsphere cultures was changed and cells were then treated with either our novel combinatorial therapy or 25 μM doxorubicin. After 48 hours spheres were harvested using a broad-tip pipette and passed through a 40 μm nylon cell strainer (BD Falcon, USA), and seeded into a 96-well plate. 20 μL of CellTiter 96® AQueous One Solution MTS (5 mg/mL) (Promega—Madison, WI, USA) was added to each well and incubated at 5% $CO_2$ at 37° C. for an additional 4 hours. Absorbance readings were taken in an Epoch microplate reader at 490 nm. Computed data was compared to untreated and normalized cells. Cells that were not administered any treatment were considered the control group. Cell viability was calculated by the following formula: Cell viability (%)=(average OD in treated group/average OD in control group)×100%.

Statistical Analysis

GraphPad Prism v8 software was used for statistical analyses. Data is presented as mean±s.d. t-test was used to determine statistical significance between groups for normally distributed data. For all tests, *$p<0.05$ was considered significant. Experiments and measurements were performed in triplicate. Graphed data depicts means of triplicates±s.e.m. and are representative of three experiments.

The data therefore reaffirms the marked resistance cancerspheres exhibit towards conventional chemotherapies, such as doxorubicin. Cancerspheres are resistant to doxorubicin treatment.

Example 7

Flow Cytometry Assay Testing of MTX+2-DG+WGN

Figure 8A:
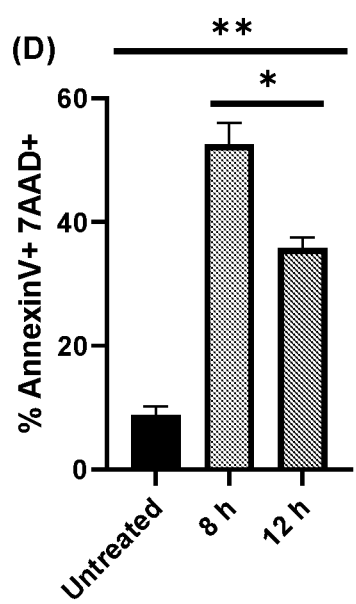
FIG. 8a is a bar graph illustrating the percent expression of annexin V and 7AAD positive readings on 4T1 cancer cells when untreated and treated with the combination of MTX+2DF+WGN at 8 hours and 12 hours.
Figure 8B:
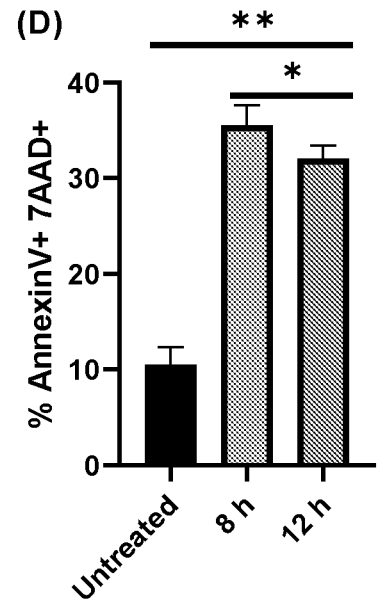
FIG. 8b is a bar graph illustrating the percent expression of annexin V and 7AAD positive readings on MCF-7 cancer cells when untreated and treated with the combination of MTX+2DF+WGN at 8 hours and 12 hours.

Flow cytometry assays were used to evaluate the effects of the combinatorial drugs MTX, 2-DG, and WGN on inducing cell death via apoptosis, the cell suicide mechanism, and necrosis. The effects of the combinatorial drugs on the expression of annexin V and 7AAD positive readings (which indicate dead cells) are illustrated in FIG. 8*a* (on 4T1 mouse breast cancer cells) and FIG. 8*b* (on MCF-7 human breast cancer cells). The combination therapy was used at concentrations 6× lower than the respective $ED_{50}$ for each individual drug. The results show the combination causes apoptosis and cell death.

Flow Cytometry

A Guava easyCyte flow cytometer with InCyte software (EMD Millipore, USA), was used to determine viability. Cells were treated with our novel combinatorial therapy for 48 hours. After 48 hours, cells were centrifuged and resuspended in 1× Annexin V binding buffer solution (BD Pharmingen, USA). 100 μL of cell suspension was transferred to a 5 mL reaction tube. 5 μL of Annexin V-FITC apoptosis detection dye (BD Pharmingen, USA) was added to the reaction tube. 10 μL of 7-AAD (BD Pharmingen, USA) nucleic acid staining dye was added to the 5 mL reaction tube. Reaction tubes were gently mixed and incubated for 15 min at RT. 400 μL of 1× binding buffer was added after incubation. Samples were then read by flow cytometry and analyzed with FlowJo v9 software. Annexin V+ and 7-AAD+ populations of treated cells were compared to Annexin V+ and 7-AAD+ populations of untreated cells.

Example 8

Flow Cytometry Testing Using PBMCs

Hundreds of thousands of anticancer compounds are screened and analyzed daily across the world. Despite their potential effectiveness against cancer cells, the vast majority fail to progress forward in the drug development process due to marked cytotoxicity towards healthy human cells. The observed cytotoxicity is primarily the result of non-specificity. The majority of clinically approved chemotherapeutic agents target DNA replicative pathways. However, normal cells are not spared from the therapeutic targeting, as some such as immune cells have been shown to proliferate faster than cancer cells. The cytotoxic effects of chemotherapeutic drugs are most notable for their immunosuppressive effects and for their toxicity to the bone marrow where hematopoietic stem cells are found.

Figure 9A:
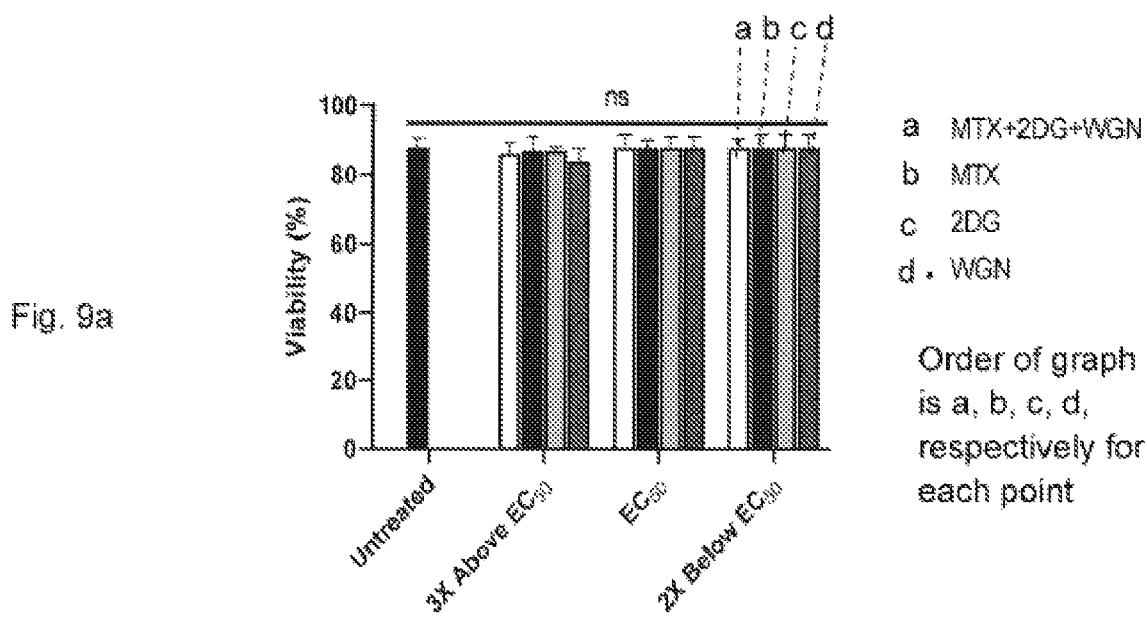
FIG. 9a is a bar graph illustrating the percent viability of quiescent peripheral-blood mononuclear cells untreated, treated with MTX, 2DF, WGN, or the combination of MTX+2-DG+WGN at 3× above ED50, at ED50, and 2× below ED50.
Figure 9B:
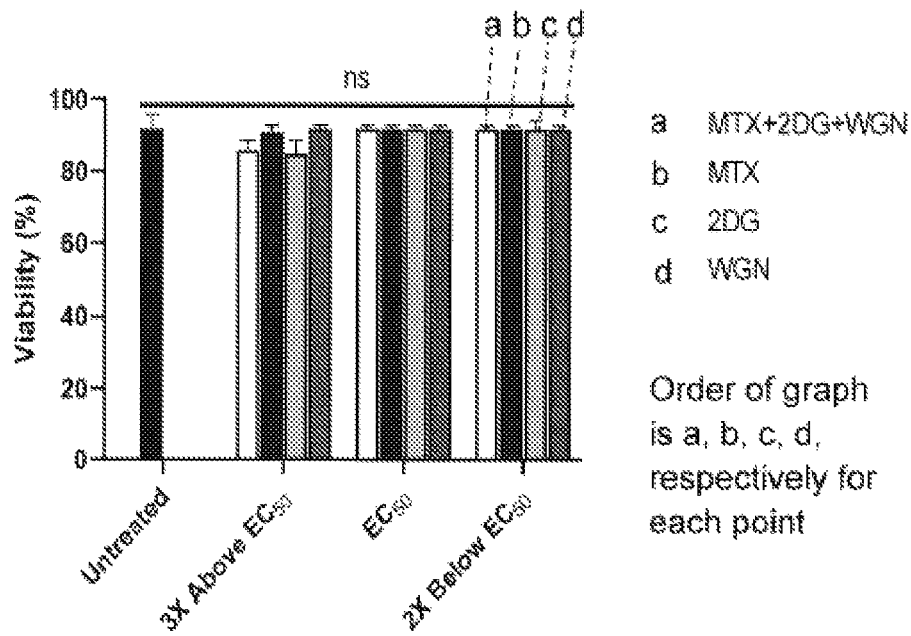
FIG. 9b is a bar graph illustrating the percent viability of quiescent peripheral-blood mononuclear cells treated with phytohemagglutinin untreated, treated with MTX, 2DF, WGN, or the combination of MTX+2-DG+WGN at 3× above ED50, at ED50, and 2× below ED50.

Conversely, the compounds in the disclosed combination are remarkably non-toxic to healthy cells and are non-mutagenic. To evaluate the effects of the combinatorial drug therapy on healthy immune cells, peripheral-blood mononuclear cells (PBMCs) were treated with the novel combinatorial therapy at concentrations 3× higher than the $ED_{50}$ dose for each compound. No significant effects on cell viability were detected whether the cells were quiescent (FIG. 9*a*) or treated with phytohaemaglutinin (PHA) (FIG. 9*b*) to stimulate their division, simulating an immune response. Division of immune cells is essential to producing an immune response.

Figure 10A:
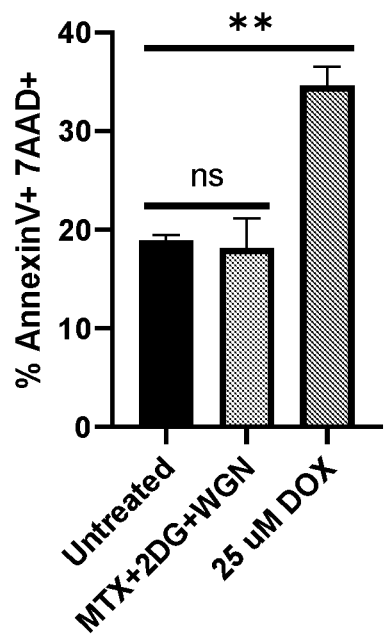
FIG. 10a is a bar graph illustrating the percent expression of annexin V and 7AAD on quiescent peripheral blood mononuclear cells when untreated, treated with the combination of MTG+2-DG+WGN or with 25 uM doxorubicin.
Figure 10B:
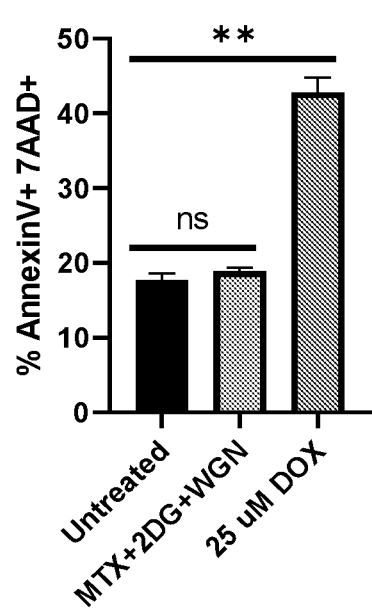
FIG. 10b is a bar graph illustrating the percent expression of annexin V and 7AAD on peripheral blood mononuclear cells treated with PHA when untreated, treated with the combination of MTG+2-DG+WGN or with 25 uM doxorubicin.

Comparison of cell death effects due to doxorubicin or the disclosed combination of drugs on healthy cells was also tested. Doxorubicin was used at its low dose in standard of care while the disclosed combination of MTX, 2-DG, and WGN was used at concentrations 3× above their respective $ED_{50}$ doses. Peripheral blood mononuclear cells were quiescent (FIG. 10*a*) or treated with PHA (FIG. 10*b*) to simulate an immune response and incubated for 48 hours Cell Culturing and Maintenance Whole blood was obtained from the OneBlood Blood Bank (Orlando, FL). Human peripheral blood mononuclear cells were derived from whole blood using Ficoll-Paque density gradient media (Cytiva, USA) and centrifugation. Cells were cultured at $1×10^6$/mL in 75 cm² Falcon cell culture flaks containing Gibco RPMI 1640-L-Glutamine medium (Life Technologies—Grand Island, NY, USA) supplemented with 10% fetal bovine serum (Life Technologies—Grand Island, NY, USA) and 100 U/mL Gibco Pen Strep (Life Technologies—Grand Island, NY, USA). Cell cultures were incubated at 37° C. under 5% $CO_2$ in a humidified atmosphere.

PHA-P Stimulation

Whole blood-derived human peripheral blood mononuclear cells were cultured at $2\times10^6$/mL in 75 cm$^2$ Falcon cell culture flaks containing Gibco RPMI 1640-L-Glutamine medium (Life Technologies—Grand Island, NY, USA) supplemented with 10% fetal bovine serum (Life Technologies—Grand Island, NY, USA) and 100 U/mL Gibco Pen Strep (Life Technologies—Grand Island, NY, USA). PHA-P was added at a final concentration of 5 µg/mL. Cell cultures were incubated at 37° C. under 5% $CO_2$ in a humidified atmosphere for 24 hours prior to treatment.

Trypan Blue Exclusion Cell Viability Assay

PHA-P stimulated human peripheral blood mononuclear cells were harvested by adding 10 mL of PBS to the flask and incubating on ice for 20 minutes. A P1000 micropipette was used to pipette 1000 µL of ice-cold PBS repeatedly. The harvested cells ($2\times10^4$ cells/ mL) were seeded in 5 mL of complete RPMI 1640 in CellTreat 15 mL Bio-reaction Cell Culture tubes, treated with the MTX, 2DG, and WGN drug combination. Cells were incubated for 48 hours at 5% $CO_2$ at 37° C. and at 48 hours post-treatment were centrifuged at 1200 RPM for 10 minutes. The resulting cell pellet was resuspended in 1 mL of complete RPMI 1640 cell culture media. 10 µL of 0.4% trypan blue was mixed with 10 µL of cell suspension in a 96-well plate well and incubated for 2 minutes at room temperature. 10 µL of the 0.4% trypan blue/cell suspension mixture was loaded onto a hemacytometer and stained vs unstained cells were counted. The percentage of viable cells was calculated.

$$\% \text{ Viability} = \frac{\text{total number of unstained cells}}{\text{total number of stained and unstained cells}} \times 100$$

Flow Cytometry

A Guava easyCyte flow cytometer with InCyte software (EMD Millipore, USA), was used to determine PBMC viability. Quiescent and PHA-stimulated PBMCs were treated with our novel combinatorial therapy for 48 hours. Cells were centrifuged and resuspended in 1× Annexin V binding buffer solution (BD Pharmingen, USA). 100 µL of cell suspension was transferred to a 5 mL reaction tube. 5 µL of Annexin V-FITC apoptosis detection dye (BD Pharmingen, USA) and 10 µL of 7-AAD (BD Pharmingen, USA) nucleic acid staining dye were added. Reaction tubes were gently mixed and incubated for 15 min at RT. 400 µL of additional 1× binding buffer was added after incubation. Samples were then read by flow cytometry and analyzed with FlowJo v9 software. Annexin V+ and 7-AAD+ populations of treated cells were compared to Annexin V+ and 7-AAD+ populations of untreated cells.

Statistical Analysis

GraphPad Prism v8 software was used for statistical analyses. Data is presented as mean±s.d. t-test was used to determine statistical significance between groups for normally distributed data. For all tests, *p<0.05 was considered significant. Experiments and measurements were performed in triplicate. Graphed data depicts means of triplicates±s.e.m. and are representative of three experiments.

Example 9

Immunogenic Cell Death Assay

The effectiveness of anticancer therapies is generally understood as the ability to directly kill cancer cells and reduce cancer mass. Recently however, additional focus has been given to the mechanism of cell death. Death by apoptosis is immunologically "quiet" meaning it does not stimulate an immune response, whereas cell death via necrosis is accompanied by the release of danger signals that recruit and activate immune cells. An important survival and proliferation strategy is for cancer cells to construct an immune barrier of anti-inflammatory immunosuppressive cells and cytokines allowing them to circumvent immunosurveillance. The induced immunosuppression blocks cell-mediated responses to the cancer cells. Lack of an adaptive immune response hampers immunological memory, making it easier for cancers to recur. Thus, a focus of all developing therapies is to induce apoptotic and necrotic cancer cell death while overcoming immunosuppression and inducing a powerful and specific anticancer immune response, known as eliciting immunogenic cell death (ICD).

Figure 11A:
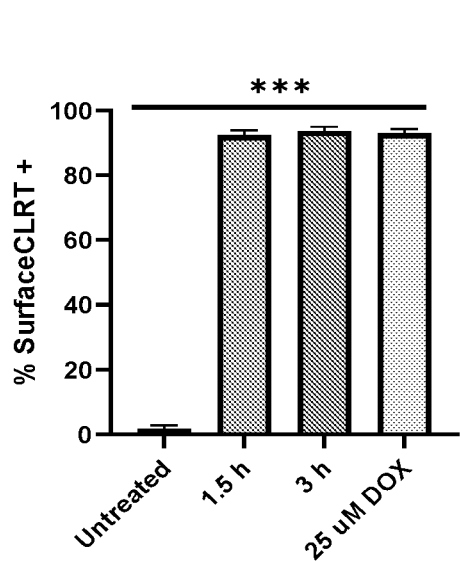
FIG. 11a is a bar graph illustrating the percentage induction of calreticulin on 4T1 cancer cells when untreated, treated with the combination of MTX+2-DG+WGN after 1.5 and 3 hours, and with 25 um doxorubicin.
Figure 11B:
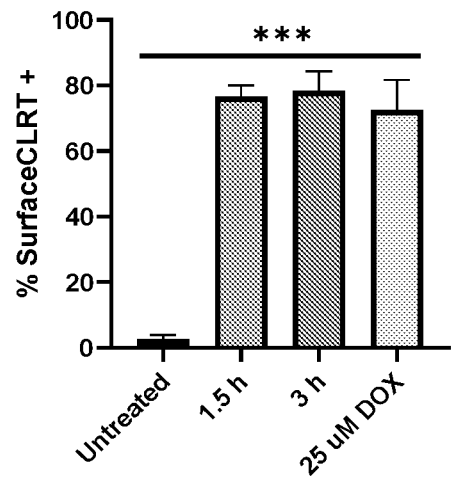
FIG. 11b is a bar graph illustrating the percentage induction of calreticulin on MCF-7 cancer cells when untreated, treated with the combination of MTX+2-DG+WGN after 1.5 and 3 hours, and with 25 um doxorubicin.
Figure 12A:
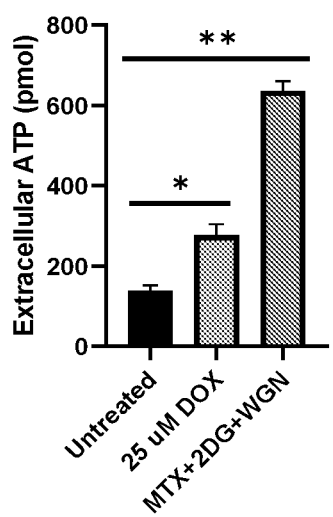
FIG. 12a is a bar graph illustrating the secretion of ATP on 4T1 cancer cells when untreated, treated with 25 um doxorubicin, and the combination of MTX+2-DG+WGN.
Figure 12B:
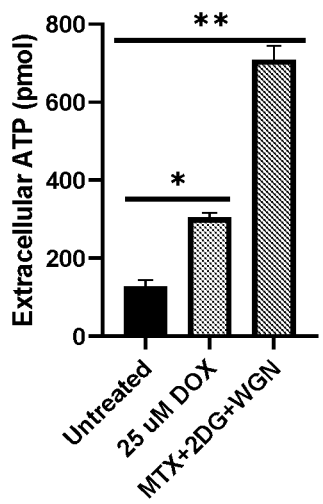
FIG. 12b is a bar graph illustrating the secretion of ATP on MCF-7 cancer cells when untreated, treated with 25 um doxorubicin, and the combination of MTX+2-DG+WGN.
Figure 13A:
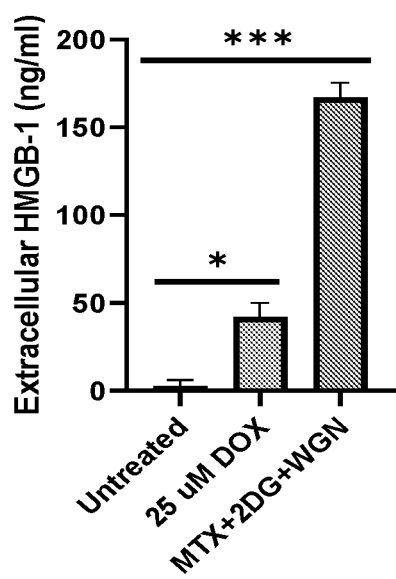
FIG. 13a is a bar graph comparing the exocytosis of HMGB-1 on 4T1 cancer cells when untreated, treated with 25 uM doxorubicin, and the combination of MTX+2-DG+WGN.
Figure 13B:
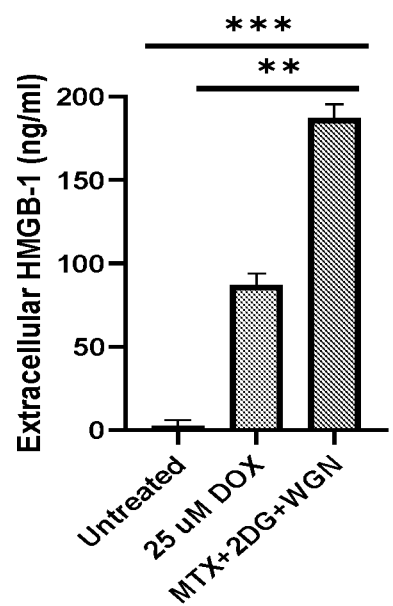
FIG. 13b is a bar graph comparing the exocytosis of HMGB-1 on MCF-7 cancer cells when untreated, treated with 25 uM doxorubicin, and the combination of MTX+2-DG+WGN.

The disclosed combinatorial therapy was shown to elicit robust ICD, evidenced by the significant detection of the three hallmarking ICD markers: calreticulin surface expression, ATP secretion, and HMGB-1 exocytosis. In all cases, the combinatorial therapy elicited an equal or greater degree of ICD-marker expression compared to doxorubicin, a known inducer of ICD. Particularly, the data illustrates a comparison of the induction of calreticulin on 4T1 mouse breast cancer cells (FIG. 11a) and MCF-7 human breast cancer cells (FIG. 11b) cells by the combination of MTX, 2-DG, and WG, along with doxorubicin. The data also provides a comparison of the secretion of ATP on 4T1 mouse breast cancer (FIG. 12a) and MCF-7 human breast cancer cells (FIG. 12b) by the disclosed combination of MTX, 2-DG, and WG and doxorubicin. A comparison of the exocytosis of HMGB-1 on 4T1 mouse breast cancer (FIG. 13a) and MCF-7 human breast cancer cells (FIG. 13b) cells using the disclosed drug combination and doxorubicin.

Cell Culturing and Maintenance

The 4-T1 (Mouse Metastatic Mammary Carcinoma) cell line was kindly donated by Dr. Vijaya Iragavarapu-Charyulu, Department of Biomedical Sciences, Florida Atlantic University. The MCF-7 (Human Metastatic Mammary Tumor) cell line was obtained from Dr. James X. Hartmann, Department of Biological Sciences, Florida Atlantic University. Cells were cultured between $2\times10^5$/mL and $1\times10^6$/mL in 75 cm$^2$ Falcon cell culture flask containing Gibco RPMI 1640-L-Glutamine medium (Life Technologies—Grand Island, NY, USA) supplemented with 10% fetal bovine serum (Life Technologies—Grand Island, NY, USA) and 100 U/mL Gibco Pen Strep (Life Technologies—Grand Island, NY, USA). Cell cultures were incubated at 37° C. under 5% $CO_2$ in a humidified atmosphere.

Flow Cytometry for CLRT-Surface Expression

A Guava easyCyte flow cytometer with InCyte software (EMD Millipore, USA), was used to analyze calreticulin surface expression in dying tumor cells. 4-T1 and MCF-7 cells cultured independently (1×10⁶ cells/tube) were treated with our novel combinatorial therapy. At 0-hour, 1.5 hour, and 3 hour time points, cells were centrifuged and resuspended in ice-cold PBS, 10% FCS, 1% sodium azide (Abcam, USA). 0.01 µg/mL of conjugated anti-calreticulin antibody was added to the reaction tube. Reaction tubes were gently mixed and incubated for 30 min at RT in the dark. Cells were washed 3 times and finally resuspended in 500 µL of ice-cold PBS, 10% FCS, 1% sodium azide. Samples were then read by flow cytometry and analyzed with FlowJo v9 software. Trypan blue exclusion was performed on all samples to ensure comparable viability to control.

The ATP Colorimetric/Fluorometric Assay Kit (Sigma-Aldrich, USA) was used to measure the levels of ATP secretion in treated tumor cell supernatant. 4-T1 and MCF-7 cells cultured independently were seeded in flat-bottom 96 well plates (1×10⁴ cells/mL) and treated with our novel combinatorial therapy. An experimental group of cells was treated with 25 µM of the known ICD-inducer doxorubicin as a positive control. 24 h post-treatment, cells were centrifuged for 20 min at 1000×g and supernatant was harvested. Fluorescence intensity unit readings were taken in a fluorescent microplate reader at $\lambda ex=535/\lambda em=587$ nm. Computed data was compared to untreated and normalized cells as well as a standard curve.

HMGB-1 ELISA

The human HMGB1 ELISA kit (Tecan Trading AG, Switzerland) was used to measure the levels of HMGB-1 in treated tumor cell supernatant. 4-T1 and MCF-7 cells were seeded independently in flat-bottom 96 well plates (1×10⁴ cells/mL) and treated with our novel combinatorial therapy. An additional experimental group of cells was treated with 25 µM of doxorubicin, a proven inducer of immunogenic cell death, as a positive control. 24 hours post-treatment, cells were centrifuged for 20 min at 1000×g and the supernatant fluid was harvested. Absorbance readings were taken in an Epoch microplate reader at 450 nm. Computed data was compared to untreated and normalized cells as well as a standard curve.

ATP Assay

Trypan Blue Exclusion Cell Count and Viability Assay

After the supernatant fluid was extracted for analysis of the above ICD studies, the resulting cell pellet was resuspended in 100 µL of complete RPMI 1640 cell culture media. 10 µL of 0.4% trypan blue was mixed with 10 µL of cell suspension in a 96-well plate well and incubated for 2 minutes at room temperature. 10 µL of the 0.4% trypan blue/cell suspension mixture was loaded onto a hemacytometer, and stained vs unstained cells were counted. The percentage of viable cells was calculated using the formula:

$$\% \text{ Viability} = \frac{\text{total number of unstained cells}}{\text{total number of stained and unstained cells}} \times 100$$

When analyzing the results in the literature for ICD values and comparing the observed results with the combination therapy, there is a robust production of ATP, exocytosis of HMGB-1, and expression of calreticulin when using our treatment, as shown in Table 2:

TABLE 2

Comparison of immunogenic cell death parameters between previous results reported in the literature and our results with the combination of three drugs

| Literature: Extracellular ATP production in MCF-7 cells | MTX + 2-DG + WGN induced Extracellular ATP production in MCF-7 cells |
|---|---|
| 450 pmol | 709 pmol |
| Literature: Extracellular HMGB1 production in MCF-7 cells | MTX + 2-DG + WGN induced Extracellular HMGB1 in MCF-7 cells |
| 150 ng/ml | 187 ng/ml |
| Literature: % cell death in MCF-7 cells | MTX + 2-DG + WGN induced cell death % |
| 40% | 37% |

CONCLUSION

The data set forth herein indicates that the disclosed combinatorial therapy is highly effective against both cancer cell monolayers and 3D models and has no cytotoxic effect towards proliferating healthy immune cells. Furthermore, treatment with the combination elicits ICD, which has the potential to prime an adaptive immune response against cancer cells and prevent against future relapse. These properties place the novel combinatorial therapy at the forefront of developing anticancer therapies.

What is claimed is:

1. A pharmaceutical formulation comprising synergistically anticancer effective amounts of:
   about 1-1000 mg/kg patient weight of 2-deoxyglucose or a pharmaceutically acceptable salt thereof;
   about 0.5-5 mg/kg patient weight of methotrexate or a pharmaceutically acceptable salt thereof;
   about 30-100 mg/kg patient weight of wogonin or a pharmaceutically acceptable salt thereof; and
   a pharmaceutically acceptable carrier.

2. The pharmaceutical formulation of claim 1, wherein the formulation comprises at least one nanoparticle delivery vehicle comprising 2-deoxyglucose, methotrexate, wogonin, or combinations thereof, wherein the nanoparticle delivery vehicles are selected from the group consisting of polymeric nanoparticles, metallic nanoparticles, liposomes, micelles, and solid lipid nanoparticles.

3. The pharmaceutical formulation of claim 1, wherein the formulation is a slow-release formulation.

4. The pharmaceutical formulation of claim 1, wherein the pharmaceutically acceptable carrier is selected from lactose, starch, glucose, methyl cellulose, magnesium stearate, mannitol, sorbitol, water, glycerol, buffer, ethanol, or combinations of distinct carriers thereof.

5. The pharmaceutical formulation of claim 1, wherein the formulation is configured as a cream, solid, liquid, powder, paste, gel, tablet, granule, foam, pack, ointment, aerosol, solvent, capsule, pill, drink, liposome, syrup, solution, suppository, emulsion, suspension, dispersion, food, beverage, bolus, electuary, paste, or other bio-delivery system or agent.

6. The pharmaceutical formulation of claim 1, further comprising one or more preservatives, buffers, stabilizers, emulsifiers, antibacterial agents, antifungal agents, wetting agents, colorings, or flavorings, each in an amount of about 0.001-5 weight percent of the formulation.

7. A kit comprising:
the pharmaceutical formulation of claim 1; and
instructions for use thereof for inhibition of cancer;
wherein the carrier is selected from lactose, starch, glucose, methyl cellulose, magnesium stearate, mannitol, sorbitol, water, glycerol, buffer, ethanol, or combinations of distinct carriers thereof.

8. The kit of claim 7, wherein the pharmaceutical formulation comprises at least one nanoparticle delivery vehicle comprising 2-deoxyglucose, methotrexate, wogonin, or combinations thereof, wherein the nanoparticle delivery vehicles are selected from polymeric nanoparticles, metallic nanoparticles, liposomes, micelles, and solid lipid nanoparticles.

9. The kit of claim 7, wherein the synergistically anticancer effective amount of 2-deoxyglucose is about 1-1000 mg/kg patient weight, the synergistically anticancer effective amount of methotrexate is about 3, 3.5, 4, 4.5, or 5 mg/kg patient weight, and the synergistically anticancer effective amount of wogonin is about 65, 70, 75, 80, 85, 90, 95, or 100 mg/kg patient weight.

10. The pharmaceutical formulation of claim 1, wherein the formulation comprises about 0.5 mg/kg patient weight of methotrexate or a pharmaceutically acceptable salt thereof.

11. The pharmaceutical formulation of claim 1, wherein the formulation comprises about 3, 3.5, 4, 4.5, or 5 mg/kg patient weight of methotrexate or a pharmaceutically acceptable salt thereof.

12. The pharmaceutical formulation of claim 1, wherein the formulation comprises about 65, 70, 75, 80, 85, 90, 95, or 100 mg/kg patient weight of wogonin or a pharmaceutically acceptable salt thereof.

13. A pharmaceutical formulation comprising synergistically anticancer effective amounts of:
about 1-1000 mg/kg patient weight of 2-deoxyglucose or a pharmaceutically acceptable salt thereof;
about 3, 3.5, 4, 4.5, or 5 mg/kg patient weight of methotrexate or a pharmaceutically acceptable salt thereof;
about 65, 70, 75, 80, 85, 90, 95, or 100 mg/kg patient weight of wogonin or a pharmaceutically acceptable salt thereof; and
a pharmaceutically acceptable carrier.

* * * * *